United States Patent
Howard et al.

(10) Patent No.: US 7,011,404 B2
(45) Date of Patent: Mar. 14, 2006

(54) SAFETY GLASSES WITH PIVOTING INTERCHANGEABLE SINGLE-LENS

(75) Inventors: Jeremy Conrad Howard, Little Compton, RI (US); Luke William Michas, Westerly, RI (US)

(73) Assignee: Bacou-Dalloz Eye & Face Protection, Inc., Smithfield, RI (US)

(*) Notice: Subject to any disclaimer, the term of this patent is extended or adjusted under 35 U.S.C. 154(b) by 59 days.

(21) Appl. No.: 10/917,117

(22) Filed: Aug. 12, 2004

(65) Prior Publication Data

US 2005/0036104 A1      Feb. 17, 2005

Related U.S. Application Data

(60) Provisional application No. 60/495,192, filed on Aug. 14, 2003.

(51) Int. Cl.
*G02C 1/00*       (2006.01)
(52) U.S. Cl. .......................... 351/83; 351/86; 351/106; 351/154
(58) Field of Classification Search ................ 351/41, 351/44, 83–88, 103–109, 124, 131–135, 351/154
See application file for complete search history.

(56) References Cited

U.S. PATENT DOCUMENTS

| | | | |
|---|---|---|---|
| 3,017,806 A | 1/1962 | Stolper | 88/41 |
| 3,453,042 A | 7/1969 | Cooper | 351/86 |
| 4,102,566 A | 7/1978 | Shelton | 351/131 |
| 4,630,321 A | 12/1986 | Sagemuehl et al. | 2/426 |
| 5,026,150 A | 6/1991 | Weber | 351/47 |
| 5,321,443 A | 6/1994 | Huber et al. | 351/47 |
| 5,357,292 A * | 10/1994 | Wiedner | 351/105 |
| D354,068 S | 1/1995 | Canavan et al. | D16/313 |
| 5,455,639 A * | 10/1995 | Magdelaine et al. | 351/47 |
| 5,526,069 A | 6/1996 | Tseng | 351/86 |
| 5,617,588 A | 4/1997 | Canavan et al. | 2/428 |
| 5,796,460 A * | 8/1998 | Maturaporn | 351/86 |
| 5,815,235 A | 9/1998 | Runckel | 351/92 |
| 5,880,806 A | 3/1999 | Conway | 351/86 |
| 5,898,469 A | 4/1999 | Wang | 351/86 |
| 5,900,922 A | 5/1999 | Moore | 351/103 |
| 5,969,787 A | 10/1999 | Hall et al. | 351/62 |

(Continued)

*Primary Examiner*—Huy Mai
(74) *Attorney, Agent, or Firm*—Barlow, Josephs & Holmes, Ltd.

(57) ABSTRACT

Eyewear having an interchangeable single lens, that can be replaced quickly and easily, is provided. The eyewear is particularly suitable for use as safety eyeglasses. The eyewear includes a unitary frame structure having an inner and outer surface. The frame includes a brow bar portion extending laterally across the brow of the wearer, a nose bridge portion depending downwardly from the brow bar, first and second outer temple portions at the outer ends of the brow bar, and lower lens frame portions. The structural frame portions are preferably molded from a relatively rigid plastic material. To provide for attachment of the lens to the frame, the first and second outer temple portions each include a molded elastomeric inset including a post-receiving aperture for receiving a complementary mounting post formed on the lens. Additionally, the nose bridge portion or the center of the brow bar may also include a locking mechanism for holding the lens in position in the central area. In some embodiments, the locking mechanism comprises a third elastomeric inset and a complementary post on the lens. In other embodiments, the locking mechanism is a channel or groove. Embodiments are disclosed wherein the lens is received against the inner surface of the frame and also against the outer surface of the lens.

20 Claims, 9 Drawing Sheets

U.S. PATENT DOCUMENTS

| | | | |
|---|---|---|---|
| 6,059,409 A | 5/2000 | Sheldon | 351/106 |
| 6,086,199 A | 7/2000 | Holland et al. | 351/86 |
| 6,132,041 A | 10/2000 | Lin | 351/105 |
| 6,164,775 A | 12/2000 | Zider et al. | 351/86 |
| 6,196,681 B1 | 3/2001 | Canavan | 351/106 |
| 6,210,001 B1 | 4/2001 | Huang | 351/86 |
| 6,227,664 B1 | 5/2001 | Pavlak | 351/62 |
| 6,241,352 B1 | 6/2001 | Metcalfe | 351/47 |
| 6,349,422 B1 * | 2/2002 | Schleger et al. | 2/431 |
| 6,386,704 B1 | 5/2002 | Wu | 351/106 |
| 6,481,845 B1 | 11/2002 | Gazzara | 351/62 |
| 6,502,938 B1 | 1/2003 | Yoshimura et al. | 351/103 |
| 6,533,412 B1 | 3/2003 | Wang et al. | 351/86 |
| 6,550,912 B1 | 4/2003 | Vitaloni | 351/47 |
| 6,585,370 B1 | 7/2003 | Zelman | 351/103 |

* cited by examiner

SAFETY GLASSES WITH PIVOTING INTERCHANGEABLE SINGLE-LENS

CROSS-REFERENCE TO RELATED APPLICATIONS

This application claims the benefit of U.S. Provisional Patent Application No. 60/495,192 having a filing date of Aug. 14, 2003, the entire contents of which are hereby incorporated by reference.

BACKGROUND OF THE INVENTION

The instant invention relates to safety eyewear and more particularly to safety eyewear having a single-lens that can be removed quickly and easily.

Individuals need to wear safety glasses in many different fields of work. As a result, the eyewear industry has developed a variety of safety eyewear products, and there are numerous types of safety glasses commercially available. In many cases, the industry has designed safety eyewear for use in particular work applications and environments. For example, workers in metal-machining operations wear safety eyewear designed to protect their eyes from flying metal shards and other debris. In chemical industries, workers wear safety eyewear designed to protect them from chemical splashes and spills. Also, technicians, who operate lasers, wear safety eyewear designed to protect their eyes from being exposed to light emitted from the laser. Because lasers can emit light at different wavelengths, a variety of lenses, each specifically designed for filtering light at a particular wavelength may be required.

In recent years, there has been a tremendous growth in safety regulations requiring individuals to wear safety eyewear while participating in many different activities. Many of these safety eyewear products have a single or mono-lens attached to a frame. The single-lens acts as a shield, protecting the eyes of a person wearing the eyewear. As a result of the requirements for different lenses in different environments and circumstances, customers of safety eyewear products have grown interested in eyeglasses having interchangeable lenses. In many instances, it is more cost-effective and convenient to purchase and store a variety of lenses than to purchase and store many different safety glasses. With safety eyewear containing a replaceable lens, a person can remove and install the lens based on a particular job task or other reason. For instance, a person can replace a soiled and/or damaged lens with a new lens. Also, a person can change the color and style of the lens for fashion reasons.

Some eyewear products having an interchangeable single-lens have previously been developed. For example, Canavan et al., U.S. Pat. No. 5,617,588 discloses protective goggles having a single-lens. The goggles include a rigid frame portion and a resilient face-engaging portion. The lens is releasably mounted to the frame body by outwardly facing detents located on the side walls of the lens. The detents on the lens slide into and engage slots located on the side walls of the frame.

Wang, U.S. Pat. No. 5,898,469 discloses single-lens eyewear having a curved frame with a long groove formed in its lower edge. The frame includes an opening at each end for receiving a temple bar and a position hole for receiving a screw that secures each temple bar to the frame. The single-lens contains notched portions that fit in the long groove of the frame. A screw is screwed into the position holes to connect the temple bars to the frame. The screws provide a pivot point for the temple bars.

Moore, U.S. Pat. No. 5,900,922 discloses glasses having a flexible frame containing a unitary lens. The frame includes a flexible first and second groove and nose piece. The upper and lower edges of the lens are pushed into the grooves to mount the lens. The '922 Patent indicates that no screws or other mechanical fasteners are used to mount the lens.

Hall, U.S. Pat. No. 5,969,787 discloses eyewear having a ventilated brow bar frame which is detachably secured to a single-lens. Two temple arms are pivotally attached to the brow bar frame to allow for adjustment of the pantoscopic angle of the eyewear. The lens include detents which engage ridges in the mounting sections of the frame. The lens is positioned in channels having surfaces which match the inner and outer surfaces of the lens. Also, the lens is described as preferably including a dimple which engages a hole in the lens to securely fasten the lens to the brow bar frame.

Schleger et al., U.S. Pat. No. 6,349,422 discloses protective eyewear having a facial shield that is attached to a brow bar. The '422 Patent mentions that in some embodiments the shield includes pivot pins disposed on each side of the shield which allows pivoting of the lens with respect to the bridge bar. The bridge bar further includes an extension that snaps into an opening in the shield. The bridge bar also includes side swivel sockets for receiving the pivot pins on temple bars. The pivot pins snap into the swivel holes provided in the bridge bar.

Although some conventional eyewear is made with an interchangeable single-lens, it still can be difficult to remove and replace some single-lenses efficiently in some instances. A person may need special tools to remove such a lens. Also, a person may have to grasp the lens repeatedly while attempting to remove them from the frame. This constant handling may lead to soiling or damaging of the lens. Moreover, some eyewear frames may not hold the lens securely in place during normal use.

In view of the foregoing, there is a need for improved eyewear having an interchangeable single-lens. The eyewear should hold the lens tightly within the frame during normal activities. At the same time, a person should be capable of removing and replacing the lens quickly and easily. The present invention provides such improved single-lens eyewear. These and other objects, features, and advantages of this invention are evident from the following description and attached figures.

SUMMARY OF THE INVENTION

The present invention relates to eyewear having an interchangeable single-lens that can be replaced quickly and easily. The eyewear is particularly suitable for use as safety eyeglasses.

The eyewear includes a unitary frame structure having an inner and an outer surface. The frame includes a brow bar portion extending laterally across the brow of the wearer, a nose bridge portion depending downwardly from the brow bar, first and second outer temple portions at the outer ends of the brow bar, and lower lens frame portions. The structural frame portions are preferably molded from a relatively rigid plastic material. To provide for attachment of the lens to the frame, the first and second outer temple portions each include a molded elastomeric inset including a post-receiving aperture for receiving a complementary mounting post formed on the lens. Additionally, the nose bridge portion or the center of the brow bar may also include a locking mechanism for holding the lens in position in the central area. In some embodiments, the locking mechanism comprises a third elastomeric inset and a complementary post on the lens. In other embodiments, the locking mechanism is a channel or groove. Embodiments are disclosed wherein the lens is received against the inner surface of the frame and also against the outer surface of the lens.

The lens is removably attached to either the inner surface of the frame or the outer surface of the frame by means of the post members interfittingly mating with the elastomeric receiving apertures.

The plastic unitary frame is preferably constructed using a two-shot molding process wherein the rigid and elastomeric materials are shot into the same mold and form a chemical bond during cooling such that the rigid plastic and elastomeric inserts form a unitary structure. Alternatively, an insert molding process could be utilized with the same or similar results.

The first disclosed embodiment of the eyewear positions the lens adjacent the inner surface of the frame, wherein the frame includes molded elastomeric insets on the inner surface at both outer temple portions and in the center of the nose bridge. The lens includes three complementary mounting posts on the outer surface thereof providing three points of attachment to the frame.

In a second embodiment, the frame further includes an inwardly overhanging channel structure having a groove for receiving an upper edge of the lens. The overhanging channel structure is made of a relatively elastomeric material and forms a bumper that will sit against the brow of the wearer.

In a third embodiment of the eyewear, the channel structure is replaced by bumper projections made of a relatively elastomeric material. The bumper projections extend along at least a portion of the upper brow bar. The lens includes complementary notches, extending along its upper edge, for receiving the bumper projections in interfitting relation.

In fourth and fifth embodiments, the brow bar portion of the frame includes include a relatively soft, flexible inwardly overhanging channel structure, similar to the second embodiment, but further including an integrally formed nose pad. In the fourth embodiment, the upper edge of the lens is simply received into the groove formed beneath the channel and behind the nose pads. In the fifth embodiment, the forward facing surface of the overhanging nose bridge additionally includes a small elastomeric bump and the lens includes a complementary central mounting aperture. The bump and aperture interfit to lock the lens in place.

In a sixth embodiment, the eyewear has substantially the same unitary frame structure as the above-described embodiments, except the lens is now received against the outer surface of the frame. Accordingly, the elastomeric insets are located on the outer surfaces of the frame and the lens mounting post members are located on the inner surface of the lens. Similar to the earlier embodiments, the lens posts engage the receiving apertures in the elastomeric insets so that the lens is removably attached to the outer surface of the frame.

In seventh and eighth embodiments of the eyewear, the lower lens frame members and the nose bridge portion are removed. In these embodiments, the lens is mounted to the upper frame member by means of the lens mounting posts engaging the elastomeric receiving apertures in the brow bar portion of the frame.

BRIEF DESCRIPTION OF THE DRAWINGS

The novel features that are characteristic of the present invention are set forth in the appended claims. However, the preferred embodiments of the invention, together with further objects and attendant advantages, are best understood by reference to the following detailed description taken in connection with the accompanying drawings in which:

DETAILED DESCRIPTION OF THE PREFERRED EMBODIMENTS

Referring now to the drawings, the eyewear of the instant invention is illustrated and generally indicated at 10 in FIGS. 1–8A. As will be hereinafter more fully described, the instant eyewear 10 offers a simple and cost-effective solution to the problem of changing a lens in single-lens eyewear. The eyewear 10 of this invention is described herein primarily as safety glasses, but it is understood that other eyewear such as sunglasses and goggles can also be made in accordance with this invention.

Various embodiments of the eyewear of this invention are shown in FIGS. 1–8A. Several of the figures shows different embodiments of the eyewear 10, but it should be understood that each embodiment includes similar components and encompasses the common concept and spirit of this invention.

Figure 1:
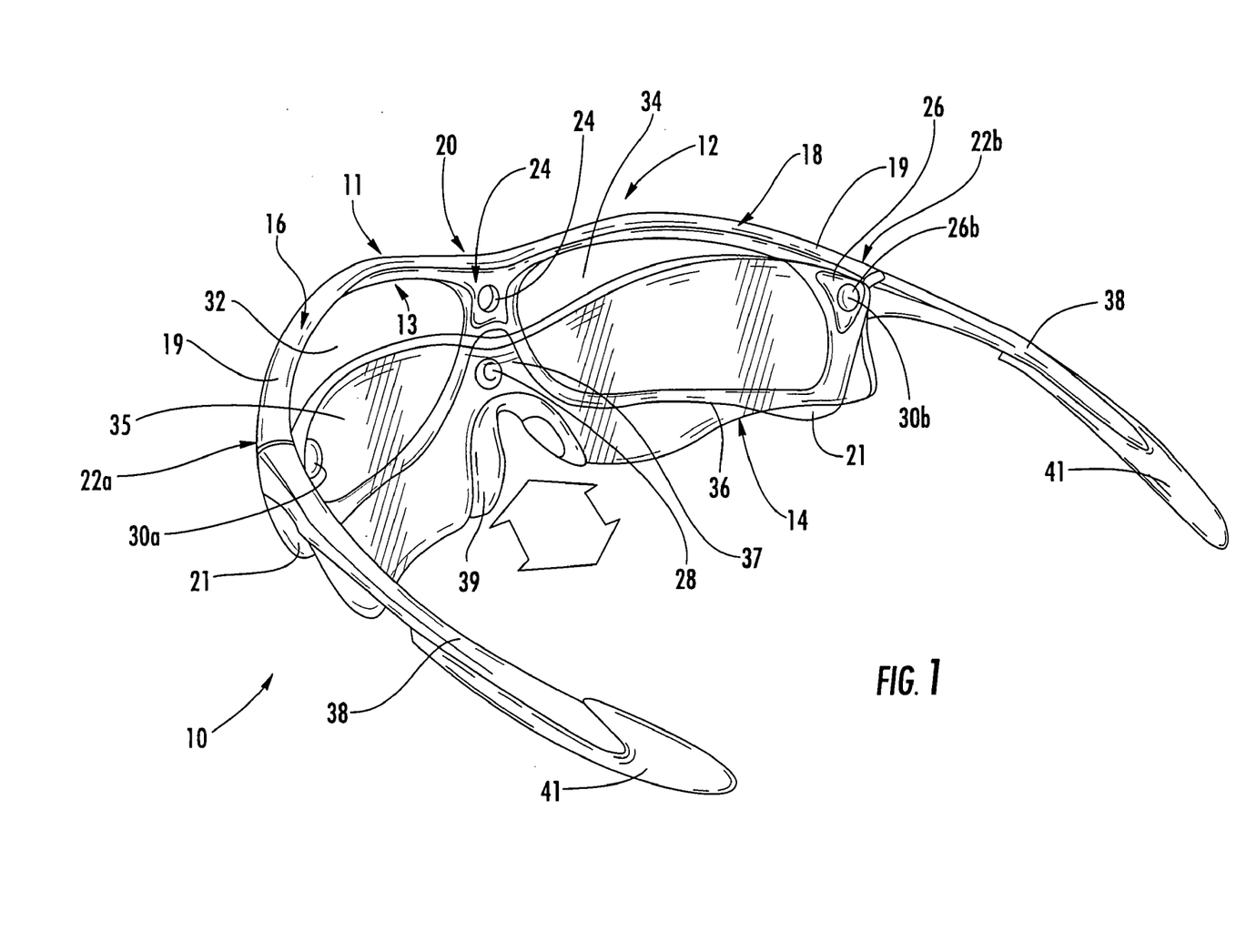
FIG. 1 is a rear perspective view of a first embodiment of an eyewear article according to the present invention.
Figure 1A:
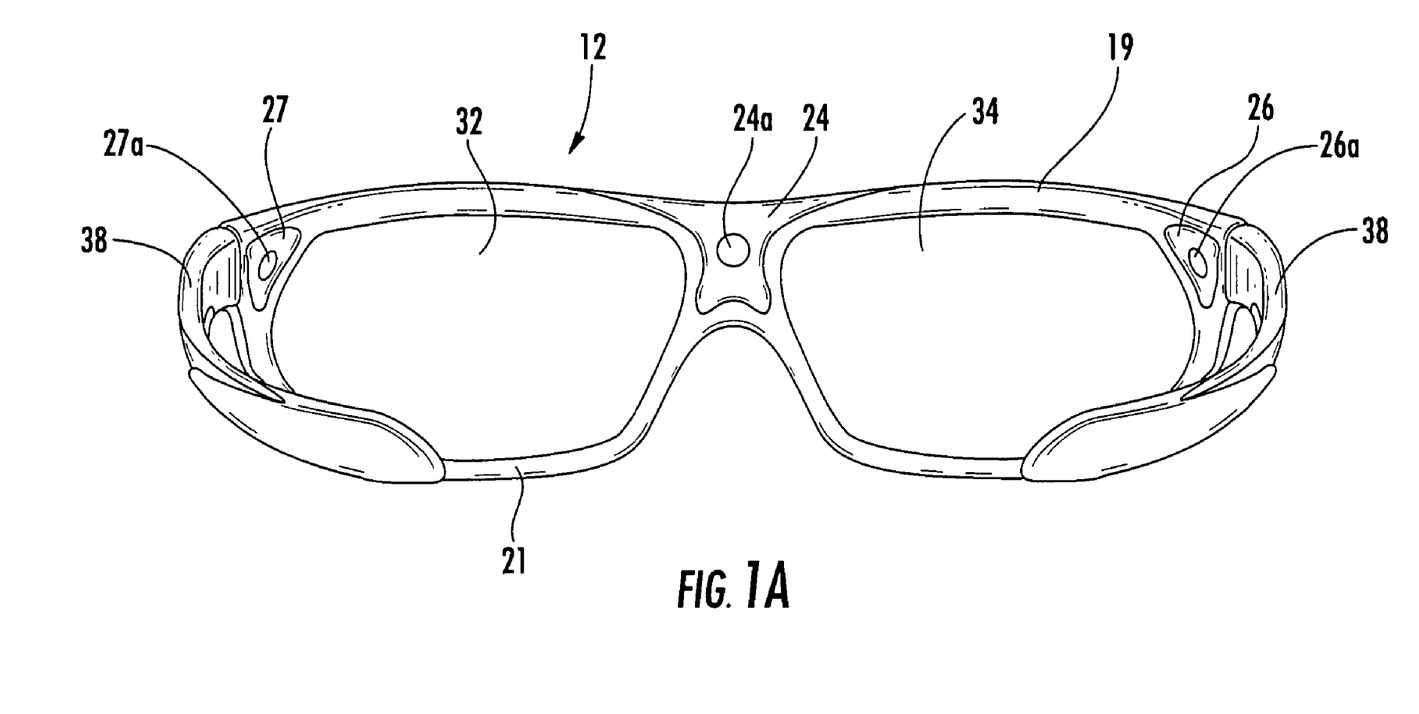
FIG. 1A is a rear plan view thereof.

The first embodiment of the safety eyeglasses 10 is shown and illustrated in FIGS. 1 and 1A. The eyeglasses 10 comprise a unitary frame generally indicated at 12 and a single unitary lens generally indicated at 14.

The frame 12 is a unitary structure preferably constructed from two different molded plastic materials as described in further detail below. The frame 12 includes an outer surface generally indicated at 11 and an inner surface generally indicated at 13. In the embodiment of FIGS. 1 and 1A, the lens 14 is shown being mounted adjacent to the inner surface 11 of the frame 12. The frame 12 generally includes a left lens frame section 16 and a right lens frame section 18.

The frame 12 includes a brow bar portion 19 extending laterally across the brow of the wearer, a nose bridge portion 20 depending downwardly from the brow bar portion 19, first and second outer temple portions 22a and 22b at the outer terminal ends of the brow bar portion 19, and lower lens frame portions 21. The structural frame portions are preferably molded as a unitary piece from a relatively rigid plastic material. Thus, the frame 12 is a continuous, one-piece structure having different components. The terms, "right", "left", "upper", and "lower" and similar terms are used herein with reference to the safety glasses as if a person was wearing the glasses. These terms are used solely for illustrative purposes and should not be construed as limiting the scope of the invention.

The general concept of the invention focuses on the use of elastomeric insets in the frame, each inset including a post receiving aperture to provide a flexible friction fit mounting point for receiving mounting posts formed on a complementary lens. Broadly, to provide for attachment of the lens 14 to the frame 12, the first and second outer temple portions 22a, 22b each include a molded elastomeric inset 26, 27, each respectively including a post-receiving aperture 26a, 27a for receiving a complementary mounting post formed on the lens 14. Additionally, the nose bridge portion 20 or the center of the brow bar 19 preferably includes a locking mechanism for holding the lens 14 in position in the central area. The locking mechanism is preferably a third elastomeric inset and aperture and/or a groove for receiving the upper edge of the lens.

Turning back to the first embodiment as shown in FIGS. 1 and 1A, the inner surface of the nose bridge portion 20 also includes a molded elastomeric inset 24 including a post-receiving aperture 24a. Collectively, these receiving apertures 24a, 26a, and 27a are configured and arranged to receive complementary mounting post members 28, 30a, and 30b which are located on the lens 14 as described in further detail below.

The lens 14 is preferably molded from a durable, high impact-resistant polycarbonate material typically used to make safety lenses. It is however, recognized that other materials may be used. Furthermore, the lens 14 can be coated, colored, tinted, or the like depending on the intended use of the lens. The lens 14 generally comprises left and right lens panels 34, 36 respectively connected in the center by a nose bridge section 37. The lens 14 may further include a nose pad 39 which may be an integrally molded piece or a snap-on piece.

In this first embodiment, the lens 14 is mounted adjacent the inner surface 11 of the frame. In this regard, each lens frame section 16 and 18 has a respective lens opening 32, 34. The lens 14 is removably mounted so that the left and right panels 35 and 36 of the lens 14 are positioned respectively behind the left and right frame sections 16 and 18.

As shown in FIG. 1, the mounting configuration includes a central mounting post 28 positioned at the central nose bridge area 37 of the lens 14, as well as the mounting posts 30a and 30b positioned at the outer side areas of each of the respective lens panels 34, 36 of the lens 14. The lens 14 may include additional mounting posts, and the frame 12 may contain additional post-receiving apertures in accordance with this invention.

In assembling the eyeglasses 10 shown in FIG. 1, a person first inserts the outer lateral mounting posts 30a and 30b of the lens 14 into the receiving apertures 26a and 27a respectively at the outer temple portions 22a, 22b. Then, the lens 14 is then rotated upwardly (in upward direction of arrow) so that it aligns with the lens openings 32 and 34. Thereafter, the center mounting post 28 is inserted into the receiving aperture 24a in the nose bridge portion 20 to the lock the lens 14 in place. The mounting posts 28, 30a, and 30b on the lens 14 inter-fittingly mate with the complementary receiving apertures 24a, 26a, and 27a on the frame 12. In this manner, the lens 14 is registered properly and tightly secured to the frame 12. As an added feature, the receiving apertures 24a, 26a, and 27a can be made so that they have a diameter slightly smaller than the diameter of the lens mounting posts 28, 30a, and 30b. This geometric configuration allows the mounting posts 28, 30a, and 30b to frictionally fit into the receiving apertures 24a, 26a, and 27a. This snug frictional fitting of the mounting posts 28, 30a, and 30b improves the stability of the mounted lens 14 and frame 12 assembly.

In removing the lens 14, a person reverses the assembly steps by disengaging the center post 28 from the receiving aperture 24a in the nose bridge portion 20; rotating the lens 14 downwardly (in downward direction of arrow); and disengaging the outer lateral posts 30a and 30b from the receiving apertures 26a and 27a.

The molded-insets 24, 26, and 27 provide the frame 12 with an improved level of elasticity so that the lens 14 can be mounted easily in the lens openings 32 and 34 and to the frame 12. Because of the elastic nature of the molded-insets 24, 26, and 27, the inset material tend to deform slightly as the lens posts 28, 30a, and 30b are inserted into the respective apertures. With this resilient deformation, the lens posts 28, 30a, and 30b can be inserted more easily into the receiving apertures 24a, 26a, and 27a. Also, the elastomeric insets 24, 26, and 27 allow for easier removal of the lens posts 28, 30a, and 30b during disassembly of the lens 14 from the frame 12.

Finally, the eyewear 10 includes left and right temple bars 38 respectively extending rearwardly from the side edges of the frame 12. The temple bars 38 are pivotally attached to the frame by pins, screws, or other conventional means. One temple bar 38 is attached to the frame 12 in the area of the first outer temple 22a, while the other temple bar 38 is attached to the frame 12 in the area of the second outer lateral portion 22b. The temple bars 38 are preferably provided with overmolded elastomeric portions 41 if desired.

In the instant invention, the entire frame structure 12, which includes brow bar member 19; nose bridge portion 20; lower lens frames 21; outer temple portions 22a and 22b; and elastomeric insets 24, 26, and 27, is preferably molded as a single-piece. In this regard, a "two-shot" molding process is preferably used to fabricate this unitary frame structure 12. This two-shot molding process is effective for forming a one-piece frame having a relatively rigid structural members while also providing elastomeric insets.

Two-shot molding processes are already known in the art for making other components of eyewear products. For example, Canavan et al., U.S. Pat. No. 5,617,588, the disclosure of which is hereby incorporated by reference, describes safety goggles having a rigid frame portion made from a hard plastic material and a resilient face-engaging portion made from a soft rubbery material. A two-shot injection molding process is used to construct the safety goggles. In Canavan, U.S. Pat. No. 6,196,681, the disclosure of which is hereby incorporated by reference, eyeglasses having a brow bar with a hard outer portion chemically bonded to a soft inner portion are described. A two-shot molding process is used to make the hard and soft portions of the brow bar.

In the instant invention, the frame 12 is made from a relatively hard, rigid material. Any suitable hard material can be used so long as it provides the frame 12 with sufficient mechanical strength and durability. For example, nylons, polyolefins, and polycarbonates can be used to make the frame 12.

In contrast to the relatively rigid structural portions of the frame 12, the insets 24, 26 and 27 of the frame 12 are made from a relatively elastomeric material. Any suitable elastomeric material can be used so long as it provides the insets 24, 26, and 27 with sufficient flexibility. For example, rubbers, silicones, thermoplastic elastomers, and other elastomeric materials can be used. The elastomeric material used to make the elastomeric insets 24, 26, and 27 is soft and pliable relative to the hard materials used to make the remaining molded portions of the frame 12. Of course, the other portions of the frame 12 also will possess some degree of flexibility, but they generally will be more rigid relative to the elastomeric insets 24, 26 and 27.

Genereally speaking, the two-shot molding process causes the relatively hard portions of the frame 12 to chemically bond to the relatively soft portions 24, 26, and 27. Different two-shot molding processes can be used. For example, in one embodiment of a two-shot molding operation, a nylon material first may be injected into a mold to form the hard frame 12. The nylon material begins curing and cooling. Then, a rubbery material, which is used to make the elastomeric portions 24, 26, and 27, is injected into the mold while the molded frame 12 is still cooling. The rubbery material of the elastomeric portions 24, 26, and 27 chemically bonds with the still uncured nylon material of the frame 12. After appropriate cooling, the unitary frame structure 12 is removed from the mold.

The resulting frame 12, is an integrally molded structure having relatively rigid structural portions and relatively elastomeric insets 24, 26, and 27 having apertures, which are adapted for receiving complementary post members 28, 30a, and 30b mounted on the lens 14. This frame construction allows a person to remove and mount the lens 14 in the eyeglasses 10 quickly and easily.

While dual-shot molding is described as the preferred process for forming the present frame 12, it is to be understood that other molding techniques, such as insert molding could also be equally effective for forming the same type of structure. In insert molding, either the elastomeric insets, or the rigid structural frame of the eyewear would first be molded in one operation and cooled, and then these already molded pieces would be inserted into a second mold to add the opposing structures. Insert molding is also a well known process in the eyewear art.

Figures 2, 2A:
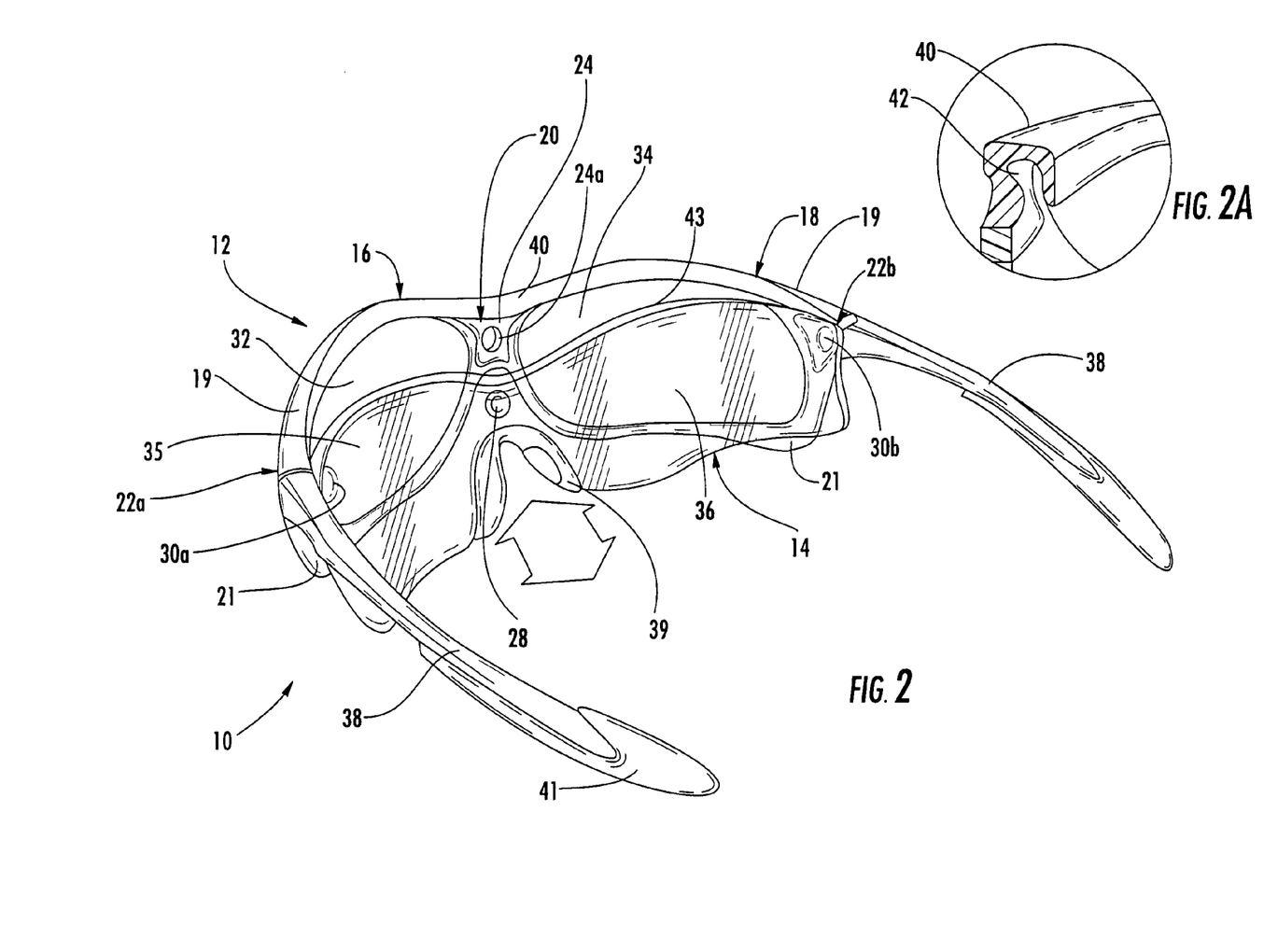
FIG. 2 is a rear perspective view of a second embodiment of an eyewear article according to the present invention.
FIG. 2A is a rear perspective and close-up view of the overhanging brow bar portion shown in FIG. 2.

Turning now to the alternate embodiments, FIG. 2 shows a second embodiment of the eyewear 10 of this invention. The eyewear in FIG. 2 has the same structure as the eyewear shown in FIG. 1, however, the frame 12 further includes an elastomeric inwardly overhanging channel structure 40 extending along the upper brow bar 19. The channel structure 40 is integrally formed as a continuation of the elastomeric inset 20, and serves to cushion the inner surface of the frame 12 while also providing a seat for receiving the upper edge 43 of the lens. Referring to FIG. 2A, the overhanging channel structure 40 is shown as having an internal groove 42 for retaining the upper edge 43 of the lens 14. As described above, the elastomeric channel structure 40 is formed as an integral extension of the inset 24 and would comprise an integrally molded component of the frame 12.

To assemble the eyeglasses 10 shown in FIG. 2, a person first inserts the outer mounting lateral posts 30a and 30b of the lens 14 into the outer lateral elastomeric receiving apertures 26a and 27a. Then, the lens 14 is rotated upwardly so that the upper edge 43 of the lens 14 slides into the internal groove 42 in the channel structure 40. Thereafter, the center post 28 is inserted into the receiving aperture 24a to lock the lens 14 in place. In this embodiment, the groove 42 further helps to align and register the lens 14 with the frame 12 as the lens is mounted to the frame 12.

Figures 3, 3A:
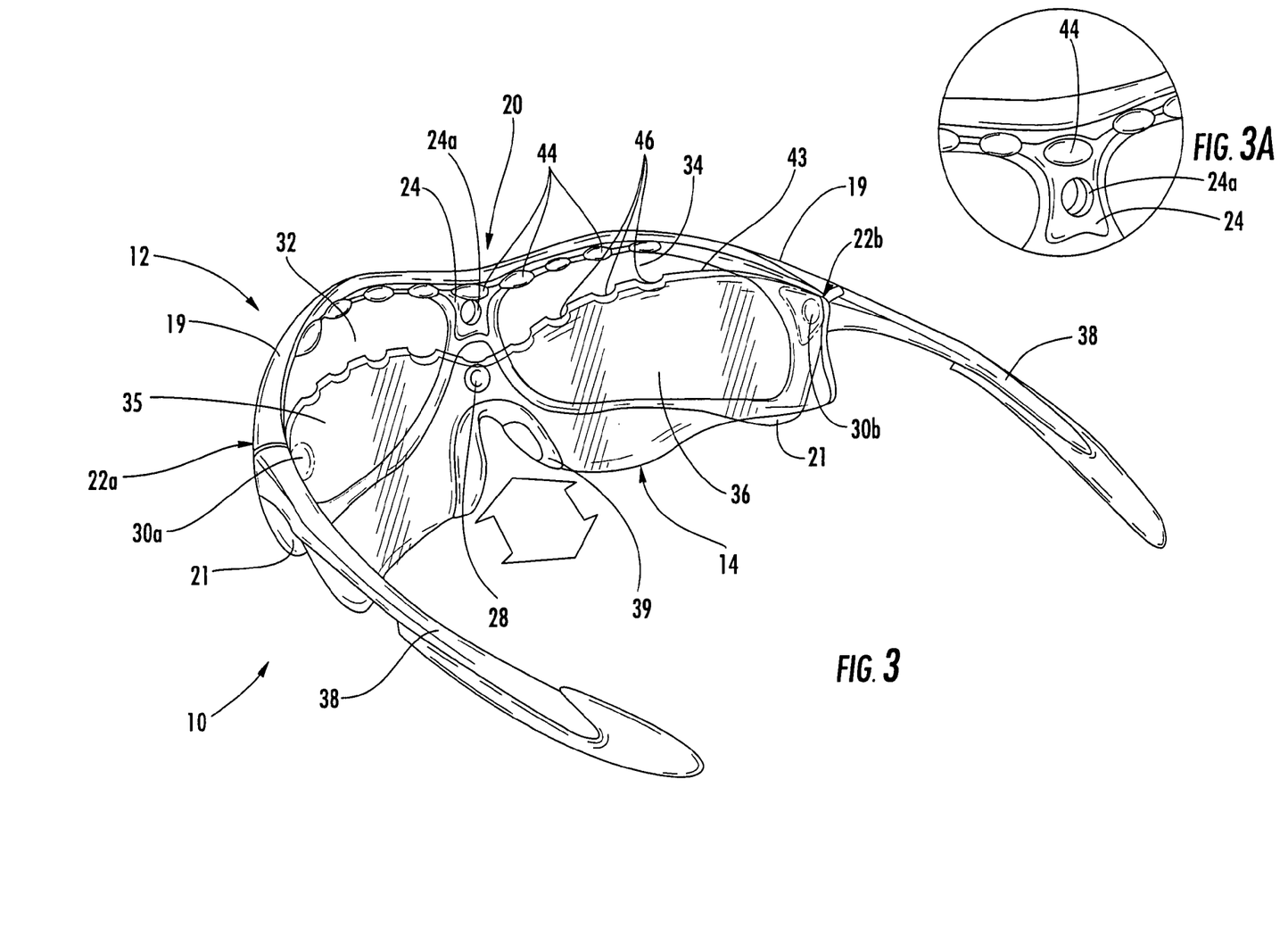
FIG. 3 is a rear perspective view of a third embodiment of an eyewear article according to the present invention.
FIG. 3A is a close-up view of the bumper projections extending along the brow bar shown in FIG. 3.

Turning now to FIG. 3, a third embodiment of the eyeglasses 10 of this invention is illustrated. The eyewear in FIG. 3 also has the same general structure as the eyewear shown in FIG. 1, however, the brow bar portion 19 of the frame 12 further includes elastomeric bumper projections 44 extending along at least a portion thereof. These soft bumper projections 44 are shown in more detail in FIG. 3A. The bumper projections 44 are preferably integrally formed as a continuation of the elastomeric inset 20, and serve to cushion the inner surface of the brow bar 19 of the frame 12 The lens 14 is provided with complementary notches 46 extending along its upper edge 43, for receiving the bumper projections 44 in interfitting relation. The bumper projections 44 fittingly engage the notches 46 as the lens 14 is mounted in the frame 12. This fitting arrangement between the bumper projections 44 and notches 46 improves the alignment and registration of the lens 14 with the frame 12. The relatively resilient bumper projections 44 are made from the same resilient materials used to make the receiving apertures 24, 26a, and 26b as described above and the resulting molded frame 12 is a unitary molded structure.

Figures 4, 4A:
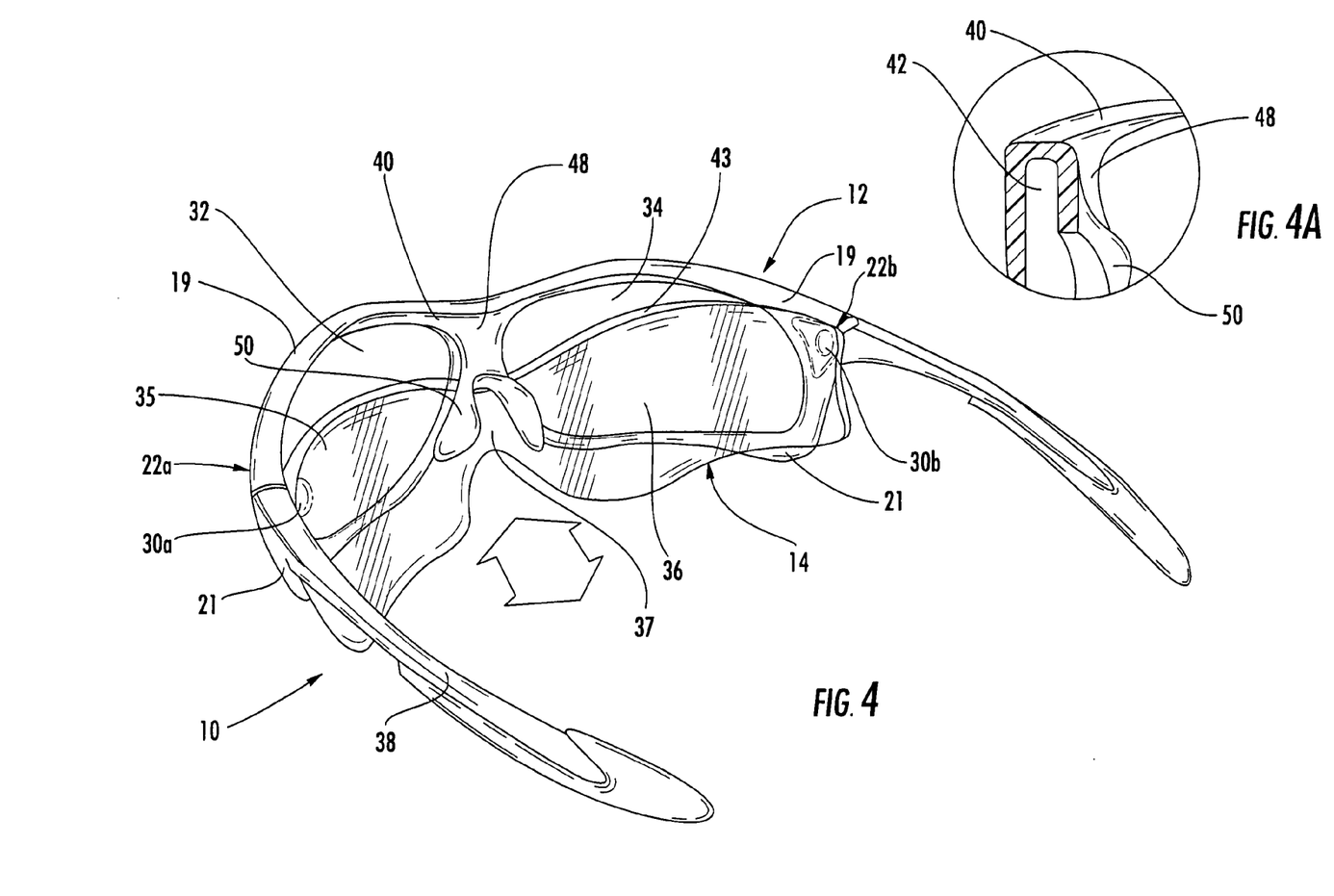
FIG. 4 is a rear perspective view of a fourth embodiment of an eyewear article according to the present invention.
FIG. 4A is a close-up view of the overhanging member and integrally formed nose pad shown in FIG. 4.

FIG. 4 shows a fourth embodiment of the eyeglasses 10 of this invention. The eyewear in FIG. 4 has the same general structure as the eyewear shown in FIG. 2, except that the inset 20 and post 28 are eliminated as a locking mechanism, and the eyeglasses 10 alternately include an integrally formed flexible bridge 48 and nose pads 50 that depend downwardly from the channel structure 40. The channel structure 40 and integrally formed bridge 48 and nose pads 50 are shown in more detail in FIG. 4A.

The channel structure 40, bridge 48 and nose pads 50 are made from the same resilient materials used to make the insets 24, 26, and 27 as described above. However, the portions of the channel structure 40 adjacent to the brow bar 19 would be an integrally molded component of the brow bar 19 using a two-shot molding process, as described above. The resulting frame 12 is a unitary molded structure that includes a relatively rigid brow bar 19 bonded to the relatively elastomeric channel structure 40.

In assembling the eyeglasses of FIG. 4, a person first inserts the outer lateral posts 30a and 30b of the lens 14 into the receiving apertures 26a and 27a. Then, the lens 14 is rotated upwardly so that it slides under the elastomeric bridge 48 and nose pad 50. As noted above, the lens 14 does not include a center post for inserting into a receiving aperture in the frame 12.

Figures 5, 5A:
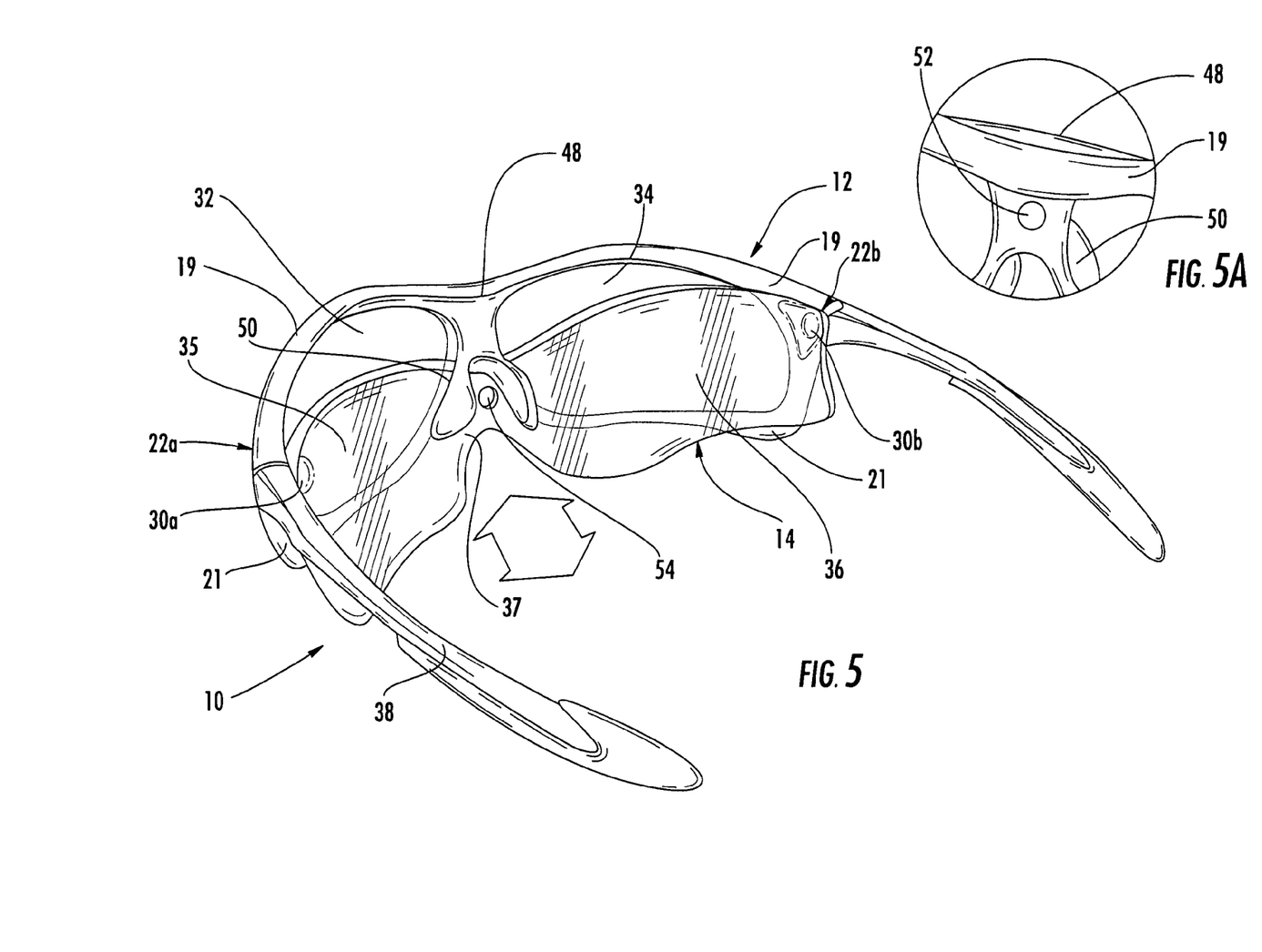
FIG. 5 is a rear perspective view of a fifth embodiment of an eyewear article according to the present invention.
FIG. 5A is a front perspective and close-up view of the overhanging member and integrally formed nose pad shown in FIG. 5.

FIG. 5 shows a fifth embodiment of the eyeglasses 10 of this invention. The eyewear in FIG. 5 has substantially the same structure as the eyewear shown in FIG. 4, except the frame 12 further includes an elastomeric bump 52 in the central nose bridge portion 20, and the lens 14 further includes a center alignment aperture 54 (FIG. 5A). In assembling the eyeglasses 10 of FIG. 5, the outer lateral posts 30a and 30b of the lens 14 are inserted into the receiving apertures 26a and 27a. Next, the lens 14 is rotated upwardly so that it slides under the elastomeric bridge 48 and nose pad 50. Then, the center aperture 54 on the lens 14 slides over the elastomeric bump 52 to lock the lens 14 in place.

In FIGS. 6–8A, different embodiments of the eyeglasses 10 of this invention are shown. The eyeglasses 10 in FIG. 6–8A have a single lens 14 that is removably attached to the outside surface 13 of the frame 12. The safety glasses 10 in FIGS. 6–8A may be desirable, because they offer better safety protection in certain environments.

Figures 6, 6A:
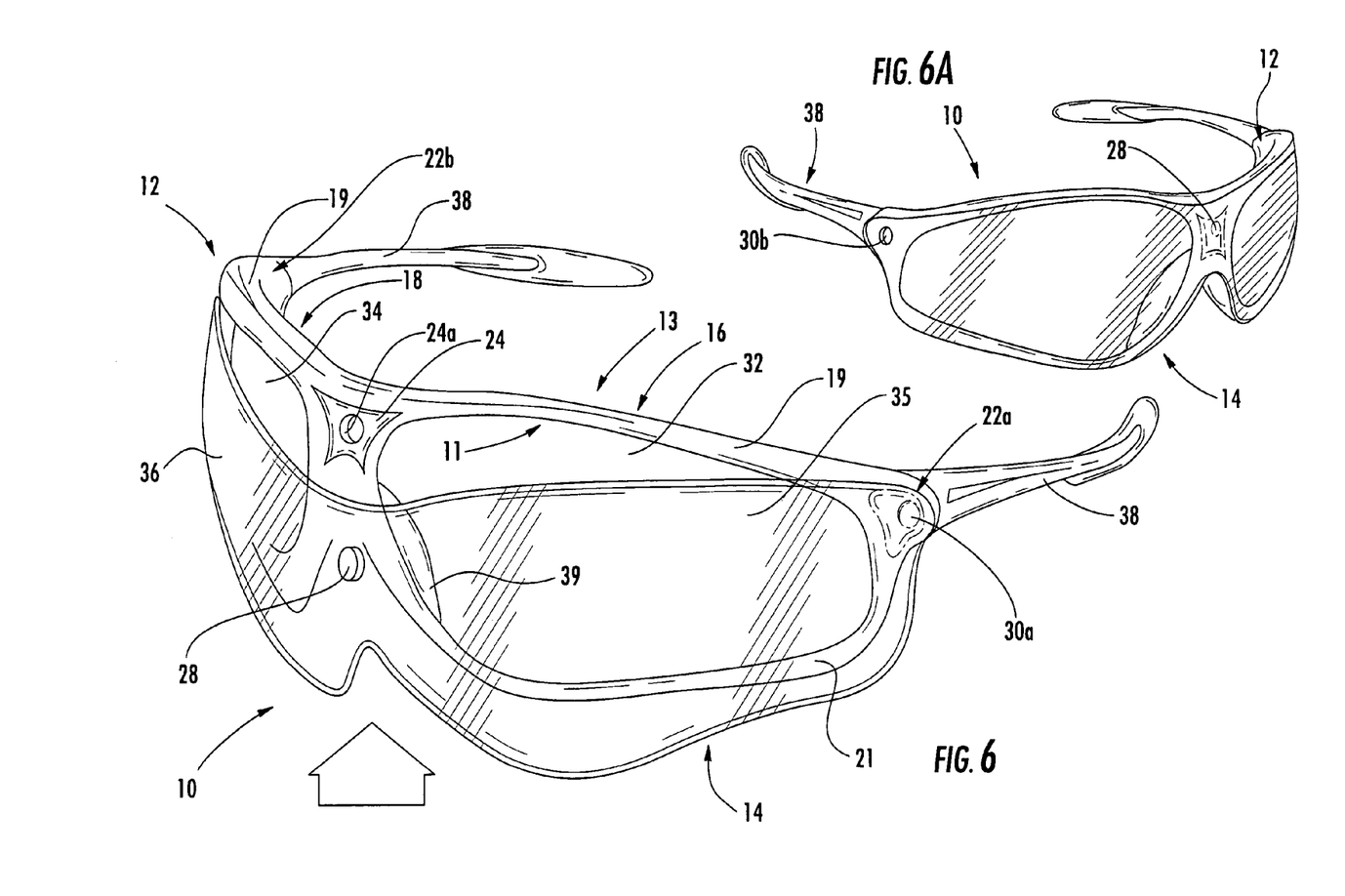
FIG. 6 is a front perspective view of a sixth embodiment of an eyewear article according to the present invention.
FIG. 6A is a front perspective view of the eyewear article in FIG. 6 showing the lens in a fully mounted position.

The frame structure shown in FIGS. 6 and 6A is substantially the same frame structure shown in FIG. 1, except the elastomeric insets 24, 26, and 267 are located on the outer surface 13 of the unitary frame 12. Accordingly, the lens mounting post members 28, 30a, and 30b are located on the inner surface of the lens 14. With this structure, a person can efficiently remove and mount a lens 14 to the outside surface 13 of the frame 12.

In assembling and disassembling the eyeglasses 10 in FIGS. 6 and 6A, a person follows essentially the same steps as described with respect to the eyeglasses 10 shown in FIG. 1. First, the person inserts the outer lateral posts 30a and 30b of the lens 14 into the elastomeric receiving apertures 26a and 27a. Then, the person rotates the lens 14 upwardly (in direction of arrow) and about the outer surface 13 of the frame 12. Then, the center post 28 of the lens 14 is inserted into the receiving aperture 24a of the nose bridge portion 20. In removing the lens 14, the assembly steps are reversed so that the center post 28 is disengaged from the receiving aperture 24a; the lens 14 is rotated downwardly and about the outer surface 13 of the frame 12; and the lateral posts 30a and 30b are disengaged from the receiving apertures 26a and 26b.

Figures 7, 7A:
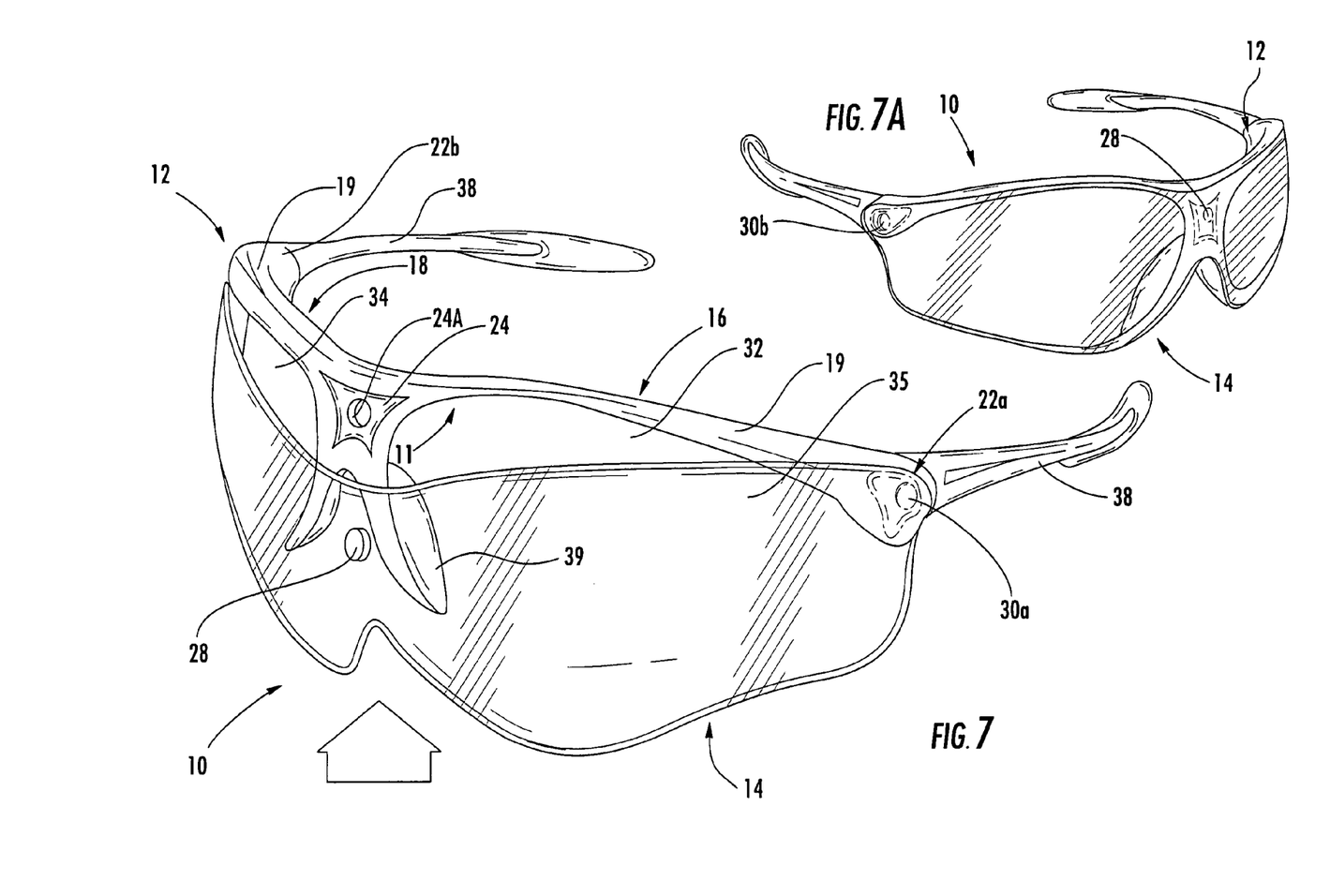
FIG. 7 is a front perspective view of a seventh embodiment of an eyewear article according to the present invention.
FIG. 7A is a front perspective view of the eyewear article in FIG. 7 showing the lens in a fully mounted position.

FIG. 7 shows a seventh embodiment of the eyeglasses 10 of this invention. The eyewear in FIG. 7 has the same structure as the eyewear shown in FIG. 6, except the frame 12 in FIG. 7 does not include a lower eye frame member 21. The absence of the lower frame member 21 gives the eyeglasses 10 in FIG. 7 a sportier look. As shown in FIG. 7, the eyewear 10 includes a nose pad 39 extending downwardly from the nose bridge portion 20. The eyewear 10 in FIG. 7 is assembled and disassembled in the same manner as the eyewear shown in FIG. 6.

Figures 8, 8A:
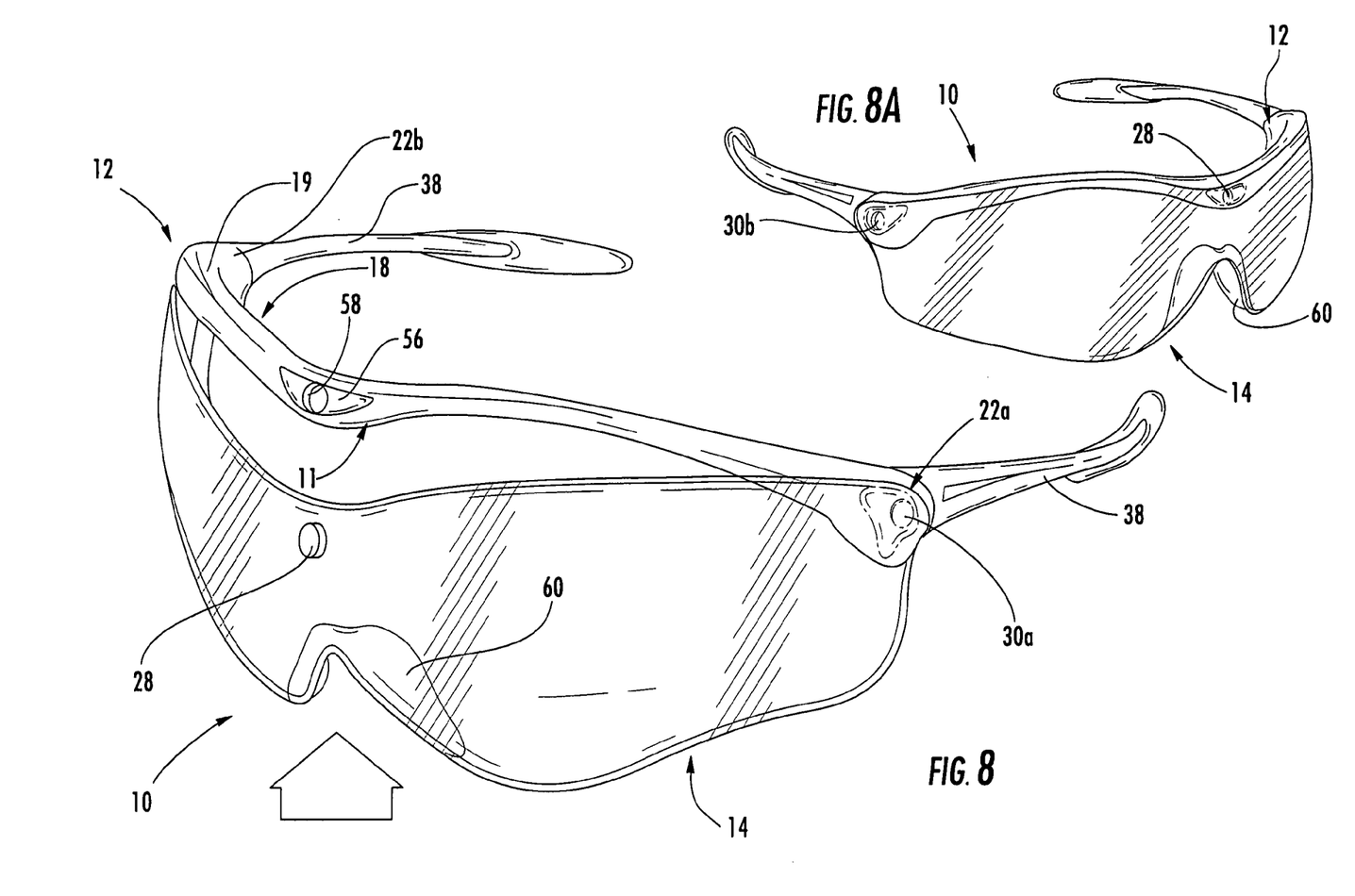
FIG. 8 is a front perspective view of an eighth embodiment of an eyewear article according to the present invention.
FIG. 8A is a front perspective view of the eyewear article in FIG. 8 showing the lens in a fully mounted position.

FIG. 8 shows an eighth embodiment of the eyeglasses 10 of this invention. The eyewear in FIG. 8 has the same structure as the eyewear shown in FIG. 6, except the frame 12 in FIG. 8 does not include a lower frame member 21 or a nose bridge portion 20. However, the brow bar 19 includes a smaller, central elastomeric inset 52 having a receiving aperture 58. In assembling the eyewear 10 of FIG. 8, the outer lateral posts 30a and 30b of the lens 14 are inserted into the receiving apertures 26a and 27a. Then, the lens 14 is rotated upwardly so that the center post 28 of the lens 14 is inserted into the central receiving aperture 58 on the brow bar 19. This action locks the lens 14 in place. As shown in FIG. 8, the lens 14 further includes a nose pad portion 60 which is an integral part of the lens 14.

It is noted that the drawings of the present invention are intended to illustrate that the elastomeric insets 24, 26 and 27 can be located on the inner surfaces, or outer surfaces in the later embodiments, and such that the apertures may or may not have a bottom. In some cases, it may be advantageous for the elastomeric insets to be molded into a seat or recess formed in the frame. In these cases, the insets would be formed on either the inner or other surface of the frame and the respective aperture would not extend entirely through the frame. It should also be understood that the elastomeric insets 24, 26, and 27, can alternately be molded so as to extend completely through the frame 12. In this regard, the inset and the aperture extending through the inset would pass entirely through the structure of the frame. In such structures, the lens 14 could potentially be mounted either on the inner surface 11 of the frame 12 or on the outer surface 13 of the frame 12. The disclosure is not intended to be limited to any one embodiment, or combination of these features.

Further still, it has been indicated above, that the present invention is also applicable to the construction of goggles as a form of eyewear. In such a proposed embodiment, the lens would incorporate the molded pins 28, 30a, 30b and the google body would be designed with respective insets 24, 26, 27 to accept and hold the pins using a softer material. The goggle body could be made using a two shot process or an insert molding process. It is also contemplated that the goggle body could be formed as a soft material only goggle body wherein the body would function as a gasket between the lens and the wearers face.

The eyewear of this invention has several advantageous features. The frame structure holds the single-lens tightly in place so that a person can participate in sports, work, and other activities. Moreover, a person can remove the single-lens and replace it with a new lens simply and quickly. No special tools are required to remove and mount the single-lens. The frame is a one-piece structure having relatively rigid portions and elastomeric insets that will deform slightly during removal and installation of the lens. The lens is equipped with complementary mounting posts so that the lens can be secured tightly to the frame.

It is appreciated by those skilled in the art that various changes and modifications can be made to the illustrated embodiments and description herein without departing from the spirit of the present invention. All such changes and modifications are intended to be covered by the appended claims.

What is claimed is:

1. Eyewear comprising:
    a unitary lens having a central bridge, an upper edge and opposing side edge portions, each of said opposing side edge portions including a respective mounting post;
    a substantially rigid frame structure including a laterally extending brow bar, and opposing temple portions at opposing ends of said brow bar,
    each of said temple portions including an elastomeric inset having a post receiving aperture therein for removably receiving a respective mounting post of said lens;
    a locking formation on said central bridge of said lens; and
    a complementary locking formation on said frame structure,
    wherein said lens is removably supported on said frame by means of said mounting posts being removably received in said respective post receiving apertures, and said locking formations being engaged in interfitting relation.

2. The eyewear of claim 1 wherein said elastomeric insets are located on an inner surface of said frame structure, and said mounting posts project outwardly from an outer surface of said lens,
    said mounting posts being received in said post receiving apertures in said elastomeric insets,
    said outer surface of said lens being received adjacent said inner surface of said frame structure.

3. The eyewear of claim 2 wherein said frame further includes a nose bridge portion depending from a central area of said brow bar, said locking formation comprising a locking post projecting from an outer surface of said lens, said complementary locking formation comprising an elastomeric inset on an inner surface of said nose bridge portion of said frame, said elastomeric inset including a post receiving aperture for receiving said locking post.

4. The eyewear of claim 3 wherein said brow bar includes an elastomeric inwardly overhanging channel structure having a groove for receiving said upper edge of said lens.

5. The eyewear of claim 3, wherein said frame further comprises a plurality of elastomeric bumper projections extending along at least a portion of the brow bar, said lens including a plurality of complementary notches extending along said upper edge of said lens, said bumper projections being received in mating formation with said notches in said lens.

6. The eyewear of claim 2 wherein said brow bar includes an inwardly overhanging channel structure having a groove for receiving said upper edge of said lens.

7. The eyewear of claim 6 wherein said overhanging channel structure is formed from an elastomeric material.

8. The eyewear of claim 6 wherein said overhanging channel structure further includes a depending nose bridge and nose pads.

9. The eyewear of claim 8 wherein an inner surface of said nose bridge includes a locking bump, and said bridge of said lens includes an aperture for receiving said bump when said upper edge of said lens is received in said groove.

10. The eyewear of claim 1, wherein said frame further comprises a plurality of elastomeric bumper projections extending along at least a portion of the brow bar, said lens including a plurality of complementary notches extending along said upper edge of said lens, said bumper projections being received in mating formation with said notches in said lens.

11. The eyewear of claim 1 wherein said elastomeric insets are located on an outer surface of said frame structure, and said mounting posts project inwardly from an inner surface of said lens,
    said mounting posts being received in said post receiving apertures in said insets,
    said inner surface of said lens being received adjacent said outer surface of said frame structure.

12. The eyewear of claim 11 wherein said frame further includes a nose bridge portion depending from a central area of said brow bar, said locking formation comprising a locking post projecting from an inner surface of said lens, said complementary locking formation comprising an elastomeric inset on an outer surface of said nose bridge portion of said frame, said elastomeric inset including a post receiving aperture for receiving said locking post.

13. The eyewear of claim 11 wherein said locking formation comprises a locking post projecting inwardly from an inner surface of said lens, and said complementary locking formation comprises an elastomeric inset on an outer surface of a central area of said brow bar, said elastomeric inset including a post receiving aperture for receiving said locking post.

14. Eyewear having an interchangeable single lens, comprising:
    a unitary frame having an inner and outer surface, the frame including a nose bridge portion, first and second temple portions, an upper brow bar and a lower lens frame member;
    the inner surface of the nose bridge portion and the first and second temple portions each having a relatively elastomeric inset having a post-receiving aperture therein, and the upper brow bar and lower lens frame member being made of a relatively rigid material; and
    a lens having complementary post members for inserting into the post-receiving apertures so that the lens is removably attached to the inner surface of the frame.

15. The eyewear of claim 14, wherein the frame further comprises an inwardly overhanging channel structure having a groove for receiving an upper edge of the lens, the overhanging channel structure being made of a relatively elastomeric material.

16. The eyewear of claim 14, wherein the frame further comprises a plurality of bumper projections extending along at least a portion of the upper frame member, the bumper projections being made of a relatively elastomeric material and wherein the lens includes complementary notches, extending along an upper edge of the lens, for receiving the bumper projections.

17. Eyewear having an interchangeable single lens, comprising:
    a frame having an inner and outer surface, the frame including a nose bridge portion, first and second temple portions, an upper brow bar, a lower lens frame, and an inwardly overhanging channel structure having an integrally formed nose pad, the overhanging channel structure being made of a relatively elastomeric material;
    the inner surface of the first and second temple portions each having a relatively elastomeric inset having a post-receiving aperture therein, and the upper brow bar and lower lens frame being made of a relatively rigid material;
    a lens having complementary mounting posts for inserting into the post receiving apertures so that the lens is removably attached to the inner surface of the frame.

18. The eyewear of claim 17, wherein the inner surface of the nose bridge portion of the frame includes a relatively elastomeric post-receiving inset and the lens includes a complementary central mounting post.

19. Eyewear having an interchangeable single lens, comprising:
    a frame having an inner and outer surface, the frame including a nose bridge portion, first and second temple portions, an upper brow bar and a lower lens frame,
    the outer surface of the nose bridge portion and the first and second temple portions each having a relatively elastomeric inset having a post-receiving aperture therein, said upper brow bar and said lower lens frame being made of a relatively rigid material; and
    a lens having complementary mounting posts for inserting into said post-receiving apertures so that the lens is removably attached to the outer surface of the frame.

20. Eyewear having an interchangeable single lens, comprising:
    a frame having an inner and outer surface, the frame including an upper brow bar, and first and second temple portions,
    the outer surface of the upper brow bar and the first and second temple portions each having a relatively elastomeric inset including a post-receiving aperture therein, the upper brow bar being made of a relatively rigid material; and
    a lens having complementary mounting posts for inserting into the post receiving apertures so that the lens is removably attached to the outer surface of the frame.

* * * * *